(12) United States Patent
Virshup et al.

(10) Patent No.: US 10,556,129 B2
(45) Date of Patent: Feb. 11, 2020

(54) SYSTEMS AND METHODS FOR TREATING A SKIN CONDITION USING RADIATION

(71) Applicant: Varian Medical Systems, Inc., Palo Alto, CA (US)

(72) Inventors: Gary F. Virshup, Cupertino, CA (US); George A. Zdasiuk, Portola Valley, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 480 days.

(21) Appl. No.: 14/874,107

(22) Filed: Oct. 2, 2015

(65) Prior Publication Data
US 2017/0095677 A1    Apr. 6, 2017

(51) Int. Cl.
*A61N 5/10* (2006.01)
*A61B 6/00* (2006.01)
*H01J 35/08* (2006.01)
*A61B 6/08* (2006.01)
*A61B 6/14* (2006.01)
*A61B 6/06* (2006.01)

(52) U.S. Cl.
CPC .............. *A61N 5/1049* (2013.01); *A61B 6/06* (2013.01); *A61B 6/08* (2013.01); *A61B 6/14* (2013.01); *A61B 6/145* (2013.01); *A61B 6/40* (2013.01); *A61B 6/46* (2013.01); *A61B 6/461* (2013.01); *A61B 6/469* (2013.01); *A61N 5/103* (2013.01); *A61N 5/1042* (2013.01); *A61N 5/1045* (2013.01); *A61N 5/1048* (2013.01); *H01J 35/08* (2013.01); *H01J 35/112* (2019.05); *H01J 35/116* (2019.05); *A61N 2005/1059* (2013.01); *A61N 2005/1074* (2013.01); *A61N 2005/1095* (2013.01)

(58) Field of Classification Search
CPC .. A61N 5/1042; A61N 5/1045; A61N 5/1048; A61N 5/1049; A61N 5/1059; A61N 2005/1074; A61N 2005/1095; A61N 2005/1059; H01J 35/08; H01J 35/112; H01J 35/116; A61B 6/06; A61B 6/08; A61B 6/14; A61B 6/145; A61B 6/40; A61B 6/46; A61B 6/461; A61B 6/469
USPC .............. 378/38–40, 65, 143, 168–170, 206, 378/145–147
See application file for complete search history.

(56) References Cited

U.S. PATENT DOCUMENTS

| 3,745,344 A | * | 7/1973 | Updegrave | A61B 6/14 378/147 |
| 3,864,576 A | * | 2/1975 | Stevenson | A61B 6/06 378/147 |

(Continued)

*Primary Examiner* — Allen C. Ho
(74) *Attorney, Agent, or Firm* — Vista IP Law Group, LLP

(57) ABSTRACT

A medical device for treating a skin of a patient includes: a radiation source configured to provide radiation; a collimator coupled to the radiation source; and an optical device for viewing a target area on the skin when a distal end of the medical device is covering the skin. A method of treating a skin of a patient includes: providing a treatment device having a distal end, a radiation source, and a collimator, wherein the distal end is configured for placement over the skin of the patient so that the skin of the patient is covered by the distal end of the treatment device; and providing an image of a target on the skin when the distal end of the treatment device is covering the skin of the patient.

25 Claims, 8 Drawing Sheets

(56) References Cited

U.S. PATENT DOCUMENTS

| | | | | |
|---|---|---|---|---|
| 3,917,954 A | * | 11/1975 | Boge | A61B 6/032 378/156 |
| 4,012,638 A | * | 3/1977 | Altschuler | A61B 6/08 250/338.1 |
| 4,104,532 A | * | 8/1978 | Weiss | A61B 6/145 378/125 |
| 4,150,296 A | * | 4/1979 | Edeland | A61B 6/14 378/170 |
| 4,166,220 A | * | 8/1979 | Stutts | A61B 6/14 378/147 |
| 4,287,423 A | * | 9/1981 | Cushman | A61B 6/14 378/168 |
| 5,068,887 A | * | 11/1991 | Hughes | A61B 6/14 378/170 |
| 5,563,923 A | * | 10/1996 | Okada | H01J 35/04 378/138 |
| 5,631,943 A | * | 5/1997 | Miles | A61B 6/145 378/102 |
| 5,692,027 A | * | 11/1997 | Yoshimura | A61B 6/14 378/116 |
| 5,708,696 A | * | 1/1998 | Kantor | A61B 6/08 378/205 |
| 5,844,962 A | * | 12/1998 | Kunert | G21K 1/04 378/150 |
| 6,036,362 A | * | 3/2000 | Schmitt | A61B 6/08 378/150 |
| 6,038,287 A | * | 3/2000 | Miles | A61B 6/14 378/117 |
| 6,229,876 B1 | * | 5/2001 | Enck | H01J 3/027 378/119 |
| 6,305,842 B1 | * | 10/2001 | Kunert | A61B 6/08 378/147 |
| 6,381,305 B1 | * | 4/2002 | Okada | H01J 35/14 378/137 |
| 6,442,237 B1 | * | 8/2002 | Corby, Jr. | G01N 23/04 378/58 |
| 6,502,984 B2 | * | 1/2003 | Ogura | A61B 6/06 378/206 |
| 6,526,122 B2 | * | 2/2003 | Matsushita | H01J 35/06 378/121 |
| 6,535,837 B1 | * | 3/2003 | Schach Von Wittenau | A61N 5/1031 378/64 |
| 6,543,936 B2 | * | 4/2003 | Feldman | A61B 6/145 378/191 |
| 6,644,853 B1 | * | 11/2003 | Kantor | H05G 1/04 378/121 |
| 6,690,761 B2 | * | 2/2004 | Lang | A61B 6/505 378/38 |
| 6,760,407 B2 | * | 7/2004 | Price | H01J 35/065 378/119 |
| 6,797,960 B1 | * | 9/2004 | Spartiotis | G01N 23/04 250/370.01 |
| 6,859,522 B2 | * | 2/2005 | Almog | A61B 6/4035 378/156 |
| 6,945,694 B2 | * | 9/2005 | Kantor | H05G 1/04 378/125 |
| 7,104,689 B2 | * | 9/2006 | Ihalainen | A61B 6/08 378/206 |
| 7,194,064 B2 | * | 3/2007 | Razzano | A61B 6/145 378/168 |
| 7,224,769 B2 | * | 5/2007 | Turner | A61B 6/14 378/102 |
| 7,247,873 B2 | * | 7/2007 | Arakawa | G01T 1/2014 250/252.1 |
| 7,278,787 B2 | * | 10/2007 | Hack | A61B 6/14 378/170 |
| 7,336,763 B2 | * | 2/2008 | Spartiotis | A61B 6/14 378/40 |
| 7,340,036 B2 | * | 3/2008 | Tomita | H01J 35/08 378/137 |
| 7,382,866 B2 | * | 6/2008 | Tan | A61B 6/06 378/147 |
| 7,413,344 B2 | * | 8/2008 | Qian | G01N 23/04 378/147 |
| 7,466,799 B2 | * | 12/2008 | Miller | H01J 35/16 378/121 |
| 7,488,109 B2 | * | 2/2009 | Hangartner | A61B 6/4035 378/168 |
| 7,496,174 B2 | * | 2/2009 | Gertner | A61N 5/1017 378/65 |
| 7,515,683 B2 | * | 4/2009 | Nanni | A61B 6/14 378/193 |
| 7,545,913 B2 | * | 6/2009 | Connelly | A61B 6/14 378/162 |
| 7,551,720 B2 | * | 6/2009 | Schick | A61B 6/14 378/191 |
| 7,620,147 B2 | * | 11/2009 | Gertner | A61N 5/10 378/145 |
| 7,664,229 B2 | * | 2/2010 | Okada | H01J 35/08 378/121 |
| 7,676,022 B2 | * | 3/2010 | Pantsar | A61B 6/14 378/38 |
| 7,680,244 B2 | * | 3/2010 | Gertner | A61N 5/1017 378/65 |
| 7,693,260 B2 | * | 4/2010 | Gertner | A61N 5/10 378/65 |
| 7,711,085 B2 | * | 5/2010 | Suzuki | A61B 6/14 378/39 |
| 7,720,199 B2 | * | 5/2010 | Inazuru | H01J 35/025 378/119 |
| 7,734,015 B2 | * | 6/2010 | Okada | H01J 35/08 378/122 |
| 7,792,249 B2 | * | 9/2010 | Gertner | A61F 9/008 378/65 |
| 7,801,271 B2 | * | 9/2010 | Gertner | A61N 5/1017 378/65 |
| 7,831,020 B2 | * | 11/2010 | Inazuru | H01J 35/04 378/136 |
| 7,929,664 B2 | * | 4/2011 | Goodenough | G01V 5/005 378/53 |
| 8,005,187 B2 | * | 8/2011 | Suzuki | A61B 6/032 378/19 |
| 8,430,563 B2 | * | 4/2013 | Uzbelger Feldman | A61B 6/14 378/191 |
| 8,506,558 B2 | * | 8/2013 | Gertner | A61F 9/008 378/65 |
| 8,821,017 B2 | * | 9/2014 | Lalena | A61B 6/08 378/206 |
| 8,827,554 B2 | * | 9/2014 | Lalena | A61B 6/46 378/206 |
| 8,890,100 B2 | * | 11/2014 | Huntzinger | G21K 1/10 250/503.1 |
| 8,903,041 B2 | * | 12/2014 | Shimizu | A61B 6/022 378/62 |
| 8,908,162 B2 | * | 12/2014 | Razzano | A61B 6/06 356/400 |
| 8,920,406 B2 | * | 12/2014 | Gertner | A61F 9/008 606/11 |
| 9,036,787 B2 | * | 5/2015 | de Jager | A61N 5/10 378/140 |
| 9,050,040 B2 | * | 6/2015 | Lee | A61B 6/145 |
| 9,125,572 B2 | * | 9/2015 | Noo | A61B 6/027 |
| 9,131,913 B2 | * | 9/2015 | Sehnert | A61B 6/469 |
| 9,161,728 B2 | * | 10/2015 | Watanabe | A61B 6/10 |
| 9,168,391 B2 | * | 10/2015 | Henning | A61N 5/1049 |
| 9,170,214 B2 | * | 10/2015 | Ferren | G01N 23/04 |
| 9,198,626 B2 | * | 12/2015 | Heuscher | A61B 6/032 |
| 9,259,191 B2 | * | 2/2016 | Noo | G21K 1/02 |
| 9,269,168 B2 | * | 2/2016 | Inglese | A61B 6/4241 |
| 9,289,268 B2 | * | 3/2016 | Ramraj | A61B 6/0457 |
| 9,314,217 B2 | * | 4/2016 | De Godzinsky | A61B 6/145 |
| 9,339,252 B2 | * | 5/2016 | Sugihara | A61B 6/032 |
| 9,351,701 B2 | * | 5/2016 | Yamakawa | A61B 6/025 |
| 9,357,971 B2 | * | 6/2016 | Yoshikawa | A61B 6/032 |
| 9,408,581 B2 | * | 8/2016 | Hyde | G21F 1/085 |
| 9,448,190 B2 | * | 9/2016 | Yun | G01N 23/2076 |

(56) References Cited

U.S. PATENT DOCUMENTS

| | | | | |
|---|---|---|---|---|
| 9,449,781 B2* | 9/2016 | Yun | .................. | H01J 35/08 |
| 9,462,985 B2* | 10/2016 | Hu | .................. | A61B 6/547 |
| 9,504,439 B2* | 11/2016 | Yi | .................. | A61B 6/5205 |
| 9,566,040 B2* | 2/2017 | Hu | .................. | A61B 6/5205 |
| 9,570,265 B1* | 2/2017 | Yun | .................. | H01J 35/14 |
| 9,592,014 B2* | 3/2017 | Melman | .................. | A61B 6/06 |
| 9,592,020 B2* | 3/2017 | Sandholm | .................. | A61B 6/469 |
| 9,594,036 B2* | 3/2017 | Yun | .................. | G01N 23/223 |
| 9,649,078 B2* | 5/2017 | Joshi | .................. | A61B 6/4405 |
| 9,668,705 B2* | 6/2017 | Yamakawa | .................. | A61B 6/14 |
| 9,697,980 B2* | 7/2017 | Ogura | .................. | H01J 35/16 |
| 9,724,052 B2* | 8/2017 | Kieft | .................. | A61B 6/06 |
| 9,743,893 B2* | 8/2017 | Inglese | .................. | A61B 6/14 |
| 9,743,901 B2* | 8/2017 | Yi | .................. | A61B 6/4035 |
| 9,782,136 B2* | 10/2017 | Zhou | .................. | A61B 6/547 |
| 9,788,805 B2* | 10/2017 | Oh | .................. | A61B 6/14 |
| 9,820,709 B2* | 11/2017 | Melman | .................. | G21K 1/04 |
| 9,823,203 B2* | 11/2017 | Yun | .................. | H01J 35/08 |
| 9,831,058 B2* | 11/2017 | Smith | .................. | H01J 5/22 |
| 9,907,530 B2* | 3/2018 | Charnegie | .................. | A61B 6/545 |
| 9,931,087 B2* | 4/2018 | Melman | .................. | G21K 1/04 |
| 9,997,269 B2* | 6/2018 | Roh | .................. | A61B 6/405 |
| 10,034,643 B2* | 7/2018 | Kim | .................. | A61B 6/469 |
| 10,039,518 B2* | 8/2018 | Kieft | .................. | A61B 6/06 |
| 10,076,293 B2* | 9/2018 | Sehnert | .................. | A61B 6/06 |
| 10,149,654 B2* | 12/2018 | Melman | .................. | A61B 6/06 |
| 10,295,485 B2* | 5/2019 | Yun | .................. | G01N 23/223 |

* cited by examiner

SYSTEMS AND METHODS FOR TREATING A SKIN CONDITION USING RADIATION

FIELD

The field of the application relates to radiation treatment, and more particularly, to systems and methods for treating a skin condition, such as skin cancer, using radiation.

BACKGROUND

Radiation therapy involves medical procedures that selectively deliver high doses of radiation to certain areas inside a human body.

In accordance with one or more embodiments described herein, a radiation system and a radiation method for treating a skin condition are provided herein.

SUMMARY

A medical device for treating a skin of a patient includes: a radiation source configured to provide radiation; a collimator coupled to the radiation source; and an optical device for viewing a target area on the skin when a distal end of the medical device is covering the skin.

Optionally, the medical device further includes a structure defining an aperture, wherein the structure is configured to couple to the collimator.

Optionally, the structure is configured to detachably couple to the collimator.

Optionally, the optical device comprises a camera.

Optionally, the camera is secured to the collimator.

Optionally, the camera is secured to an interior surface of the collimator.

Optionally, the collimator comprises a recess for accommodating the camera.

Optionally, the medical device further includes a fiber optic bundle coupled to the camera, wherein the fiber optic bundle is secured to the collimator.

Optionally, the camera is located outside the collimator.

Optionally, the medical device further includes a light source for providing light to a space located inside the collimator when the collimator is placed over the skin.

Optionally, the light source comprises a light bulb.

Optionally, the light bulb is secured to the collimator.

Optionally, the light source comprises a fiber optic.

Optionally, the medical device further includes a flattening filter coupled to the collimator.

Optionally, the flattening filter is made from a transparent material.

Optionally, the flattening filter has a mirror surface.

Optionally, the flattening filter is placed perpendicular with respect to a beam axis of the radiation source.

Optionally, the flattening filter is placed at an acute angle with respect to a beam axis of the radiation source.

Optionally, the radiation source comprises a longitudinal axis, and wherein the radiation source comprises an anode and a cathode that is located offset from the longitudinal axis.

Optionally, the radiation source comprises a window for outputting the radiation, and wherein the collimator has an opening that is aligned with the window of the radiation source.

Optionally, the collimator has a first end, a second end, and a longitudinal axis extending between the first end and the second end, and wherein the collimator further comprises a channel with a cross sectional dimension that increases along at least a part of the longitudinal axis.

A method of treating a skin of a patient includes: providing a treatment device having a distal end, a radiation source, and a collimator, wherein the distal end is configured for placement over the skin of the patient so that the skin of the patient is covered by the distal end of the treatment device; and providing an image of a target on the skin when the distal end of the treatment device is covering the skin of the patient.

Optionally, the treatment device further comprises a structure defining an aperture, the structure coupled to the collimator.

Optionally, the method further includes using the radiation source to deliver treatment radiation at the target on the skin.

Optionally, the method further includes providing one or more additional images of the target when the target is being treated by the radiation.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
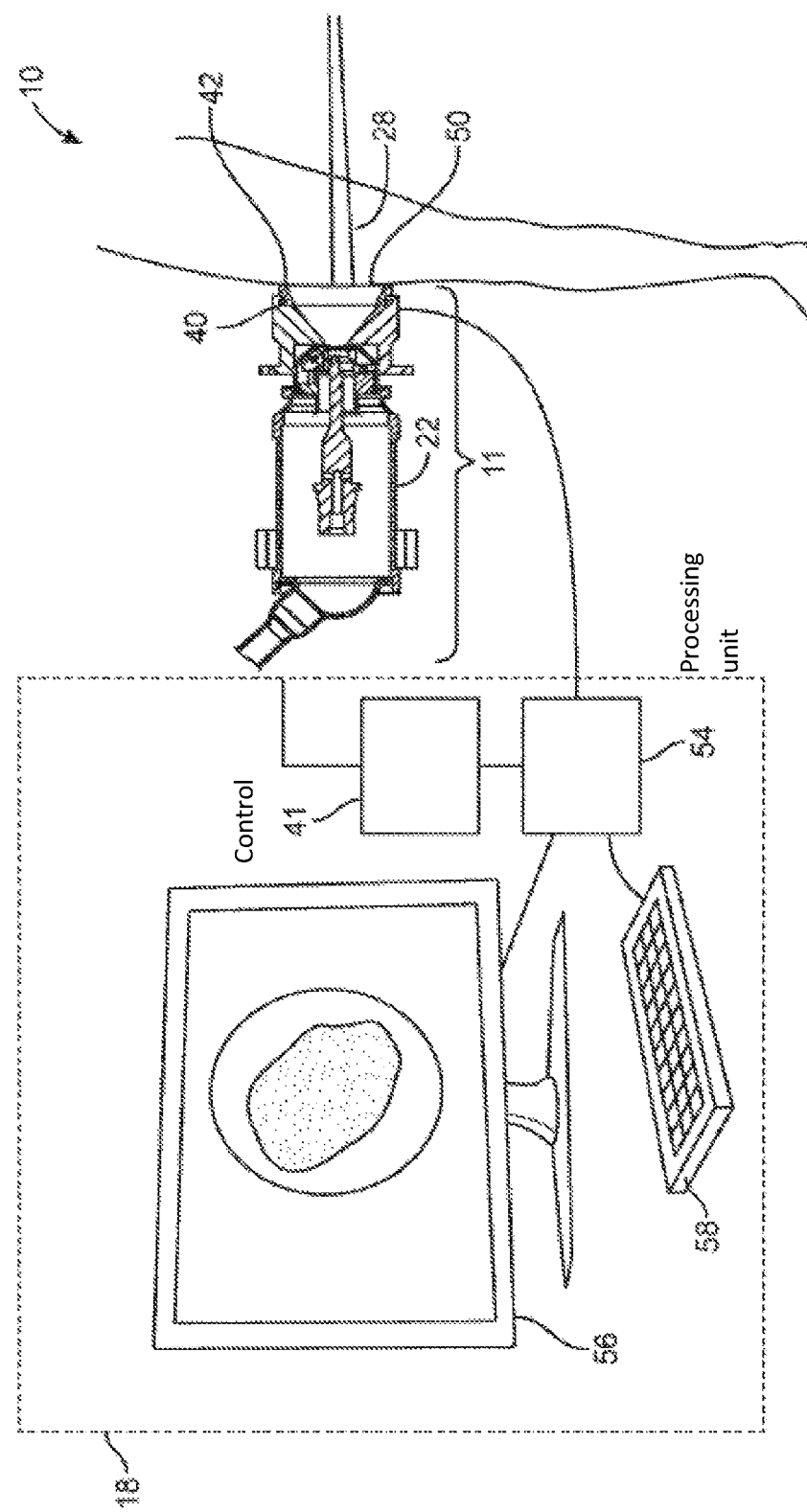
FIG. 1 illustrates a radiation treatment system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10 for treating skin of a patient. The radiation treatment system 10 includes a control system 18, a radiation source 22 that projects a beam of radiation towards the skin 28 of the patient, a collimator 40, a structure 42 defining an aperture 44 for allowing radiation to exit therethrough, and a camera system 50. The radiation source 22 may be configured to generate a cone beam, a fan beam, or other types of radiation beams in different embodiments. The control system 18 is configured to control an operation of the radiation source 22.

In the illustrated embodiments, the radiation source 22, the collimator 40, and the structure 42 are parts of a radiation treatment device 11 that is moveably mounted to a support, which allows the radiation treatment device 11 to be adjustable in position relative to the patient. For example, the radiation treatment device 11 may be translatable in one axis, or multiple axes (e.g., x, y, and z axes) that are perpendicular to each other. Also, the radiation treatment device 11 may be rotatable in one or more axes. In other embodiments, the radiation treatment device 11 may have other form and/or configuration. For example, in other embodiments, the radiation treatment device 11 carrying the radiation source 22, the collimator 40, and the structure 42 may be in a form of a hand-held device that allows a physician to desirably position the radiation treatment device 11.

In the illustrated embodiments, the radiation source 22 is a treatment radiation source for providing treatment energy. In some embodiments, the treatment energy is generally those energies of 30 kilo-electron-volts (keV) or greater, and more preferably 50-70 keV. In one implementation, the radiation source 22 may be a VF-50 x-ray tube (e.g., 50 W, 50 kVp x-ray tube), available at Varian, Palo Alto, Calif. Such x-ray tube has a tungsten anode. However, other types of x-ray tube may be used to implement the radiation source 22. For example, in other embodiments, the radiation source 22 may have other anodes made from other materials other than tungsten.

In the illustrated embodiments, the control system 18 includes a processing unit 54, such as a processor, coupled to a control 41. The control system 18 may also include a monitor 56 for displaying data and an input device 58, such as a keyboard or a mouse, for inputting data. The operation of the radiation source 22 may be controlled by the control 41, which provides power and timing signals to the radiation source 22. Although the control 41 is shown as a separate component from the processing unit 54, in alternative embodiments, the control 41 can be a part of the processing unit 54.

In some embodiments, the control system 18 may also include a treatment planning system.

Figure 2A:
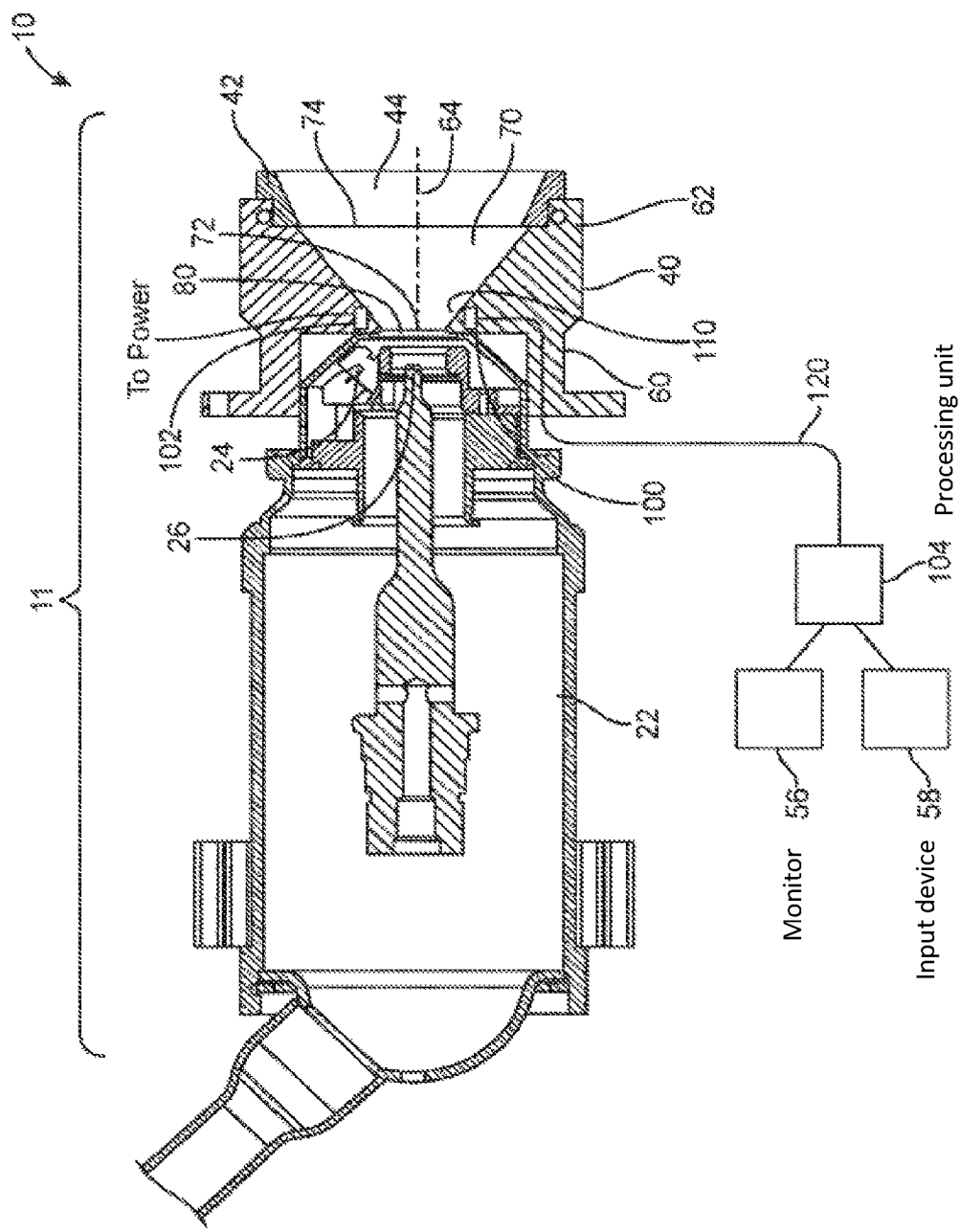
FIG. 2A illustrates the radiation treatment system of FIG. 1, particularly showing a collimator with an optical device.

FIG. 2A shows an exploded view of the radiation source 22, the collimator 40, the structure 42 defining the aperture 44, and the camera system 50 of the radiation treatment system 10 of FIG. 1. The radiation source 22 includes a cathode 24 and an anode 26. As shown in the figure, the cathode 24 is located offset from the longitudinal axis 64 of the radiation source 22. An electron gun may be used to generate an electron beam using the cathode 24. The electron beam strikes the surface of the anode 26 to generate x-rays that emanate through window 80. In some cases, the anode 26 may be rotating when the electron beam strikes its surface. In some embodiments, the radiation source 22 may have a small size, and may weigh less than 5 lbs. In other embodiments, the radiation source 22 may have any size, and may weigh more than 5 lbs.

The collimator 40 along with the structure 42 defining the aperture 44 is configured to direct and isolate the x-rays from the radiation source 22 so that the area of the skin 28 to be irradiated by the radiation beam is limited. As shown in FIG. 2A, the collimator 40 has a first end 60, a second end 62, and a longitudinal axis 64 extending between the first end 60 and the second end 62. The collimator 40 has a channel 70 with a cross sectional dimension that increases at least partially along the axis 64. In particular, the channel 70 of the collimator 40 extends from a first opening 72 at or near the first end 60, to a second opening 74 at or near the second end 62, with the second opening 74 being larger than the first opening 72. In some cases, if the cross sectional shape of the channel 70 is circular, then the channel 70 may have a shape that resembles a partial cone.

In the illustrated embodiments, the structure 42 defining the aperture 44 is detachably coupled to the collimator 40. As shown in the illustrated embodiments, the collimator 40 and the structure 42 may be considered as both being located at the distal end of the treatment device 11. In some cases, there may be a plurality of available structures 42 defining respective apertures 44 having different respective dimensions (e.g., cross-sectional dimensions of the apertures 44) and/or shapes. For example, the different structures 42 may define apertures 44 with cross-sectional dimensions ranging from 5 mm to 7 cm. During treatment, one of the available structures 42 is selected, and is detachably coupled to the collimator 40. The selection may be made based on the size of the tumor to be treated. In other embodiments, the structure 42 may be permanently secured to the collimator 40, and may be considered to be a part of the collimator 40. In further embodiments, the radiation treatment system 10 may not include any structure 42.

As shown in FIG. 2A, the radiation source 22 has a window 80 for allowing x-ray beam to exit there through. The window 80 of the radiation source 22 is aligned with the first opening 72 of the collimator 40 and the structure 42 defining the aperture 44. The collimator 40 together with the structure 42 is configured to constrain the x-ray treatment to the area of the skin 28 which the physician wants to treat with the x-ray. The alignment of the first opening 72 with the collimator 40 including the structure 42, and the target to be treated, is important. If the collimator 40 with the structure 42 defining the aperture 44 is misaligned, then the radiation will miss the treatment area, and the patient may not receive the full benefit of the treatment.

Also as shown in FIG. 2A, the camera system 50 includes a camera 100 (an example of an optical device), a light source 102, and a processing unit 104 configured to process images from the camera 100. The processing unit 104 may also be configured to output information for display on a screen 56. In the illustrated embodiments, the processing unit 104 is a separate component from the processing unit 54 that controls the operation of the radiation source 22. In other embodiments, the processing unit 104 may be combined, or implemented in, the processing unit 54. The camera 100 may be a color camera, or a black-and-white camera. In the illustrated embodiments, the camera 100 is mounted to the collimator 40. The collimator 40 has a recess 110 for accommodating the camera 100. The collimator 40 also has a channel for accommodating at least a part of a cable 120 connecting the camera 100 to the processing unit 104. Also, in some embodiments, the camera 100 may be mounted to an interior surface of the collimator 40. Also, in the illustrated embodiments, the light source 102 is a light bulb mounted at the collimator 40. The light bulb may be a LED light bulb, an incandescent light bulb, or any of other types of light bulbs. Also, in other embodiments, instead of a single light bulb, the camera system 50 may include multiple light bulbs mounted to the collimator 40. The collimator 40 also includes a channel for accommodating electrical wiring connecting the light bulb to an electrical power source.

During use, when the collimator 40 and the structure 42 is placed over the skin 28 of the patient so that the target area on the skin 28 is defined by the collimator 40 and the structure 42, the light source 102 is energized by the electrical power source to provide light to the space confined by the collimator 40 and the structure 42. The electrical power source may be located at the radiation source 22, or coupled to another component that is a part of the radiation treatment system 10. After the space confined by the collimator 40 and the structure 42 is illuminated by the light source 102, the camera 100 is then used to capture an image of the skin area that is being defined by the aperture 44 of the structure 42. The image is transmitted as image signals via the cable 120 to the processing unit 104. The processing unit 104 processes the image from the camera 100, and generates an output.

In some embodiments, the output from the processing unit 104 may be image signals that are formatted for display on the screen 56, so that a physician can see the image of the skin area that is being defined by the aperture 44 of the structure 42. This feature is advantageous because it allows the physician to visualize and verify the area of the patient to be treated by the radiation. The ability to visualize the inside of the collimator 40 and the patient's skin 28 covered by the collimator 40 and the structure 42 is important to make sure that the radiation source 22 is properly aligned to the target region prescribed for treatment.

In other embodiments, in addition, or in the alternative to, image signals, the processing unit 104 may output a signal to indicate whether the radiation treatment system 10 has been desirably positioned relative to the patient. In one implementation, the processing unit 104 may be configured to compare the current image with a reference image (such as that obtained during a setup or planning procedure). If the current image matches the reference image, then the processing unit 104 may generate an output indicating that the position of the radiation treatment system 10 relative to the patient is correct. For example, the processing unit 104 may generate an output to cause a speaker to provide an audio signal indicating that the radiation treatment system 10 is positioned correctly, or incorrectly, with respect to the patient. The processing unit 104 may also generate an output to cause a visual indicator to be provided, which indicates whether the radiation treatment system 10 is positioned correctly with respect to the patient, or not. The visual indicator may be one or more LEDs, or visual information displayed on a screen.

After the radiation treatment system 10 is desirably positioned with respect to the patient, the radiation source 22 is then activated to deliver radiation to treat the target at the skin 28. By means of non-limiting examples, the treatment may be for treating cancerous tissue at the skin 28, for treating cancerous tissue underneath the skin 28, or for cosmetic purposes.

Also, in some embodiments, the camera 100 and the light source 102 may continue to be operated during the operation to provide feedback to the physician. For example, during a treatment delivery session to deliver radiation towards the target at the skin 28 of the patient, the light source 102 may remain on, and the camera 100 may continue to monitor the position of the target at the skin 28. If the patient moves, or if the radiation treatment system 10 moves, so that the target on the skin 28 is no longer at the desired position, the processing unit 104 can detect such movement, and may generate a signal to indicate such to the physician. As similarly described, the signal may be output by the processing unit 104 to cause a visual signal and/or audio signal to be provided. In one implementation, the processing unit 104 may continue to process real-time images obtained by the camera 100 during the treatment session to determine if the target on the skin 28 is at the desired position or not. For example, the processing unit 104 may compare each real-time image, or every nth real-time image, with a reference image. The comparison may be implemented by performing imaging processing to compare images. One technique is to perform cross-correlation between the real-time image with the reference image. If the target stays in the same position as that in the reference image, then the real-time image would be substantially identical to the reference image, and the cross-correlation would indicate that there is a high correlation between the real-time image and the reference image. The reference image may be obtained during a treatment planning, or during a treatment session (e.g., during a patient setup procedure, or between radiation deliveries). If the comparison indicates that the target is shifted out of the desired position, then the processing unit 104 may generate a signal to inform the physician.

Figure 2B:
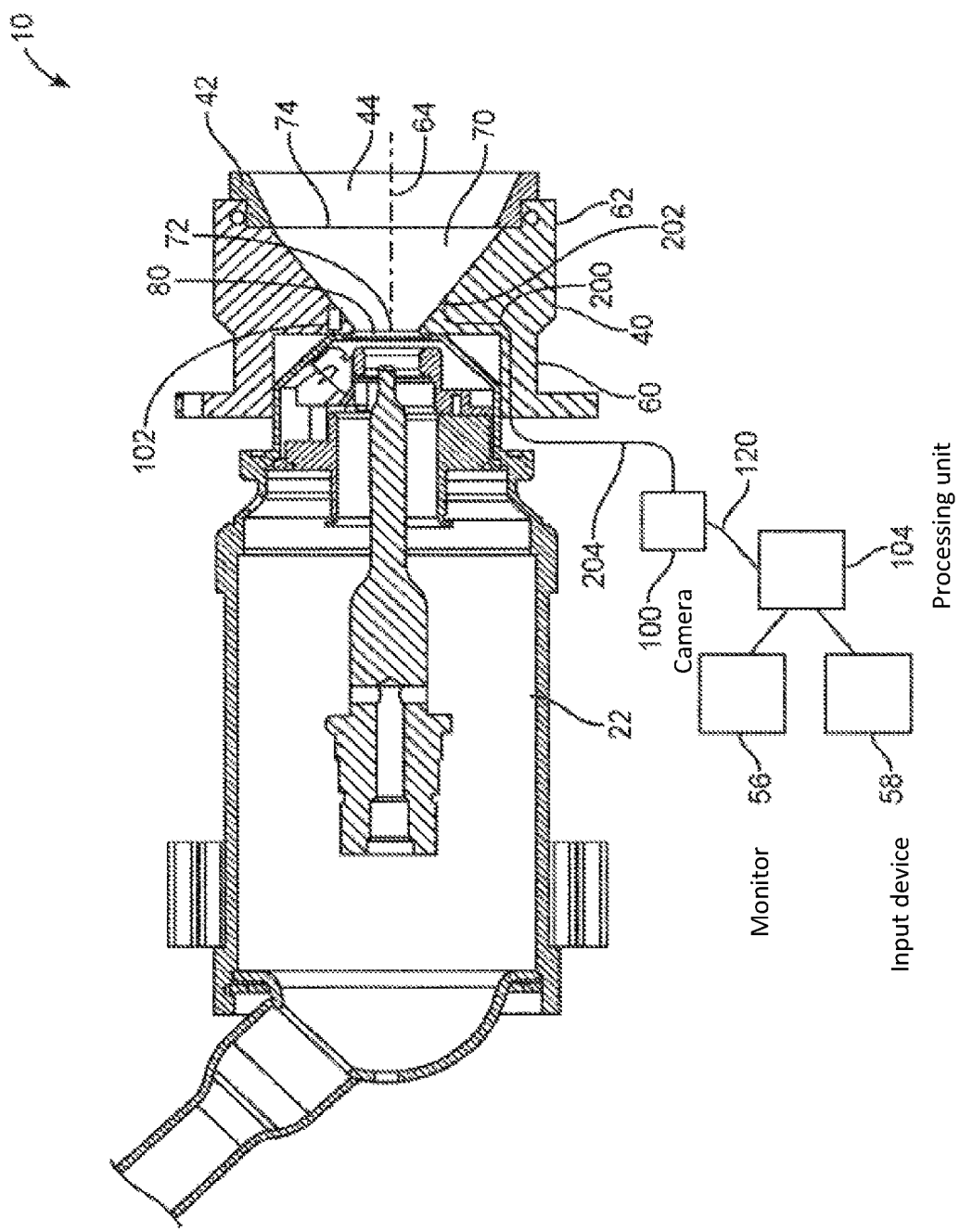
FIG. 2B illustrates another radiation treatment system.

In the above embodiments, the camera 100 is described as being attached to the collimator 40. In other embodiments, the camera 100 may be located outside the collimator 40. For example, as shown in FIG. 2B, in other embodiments, instead of having the camera 100 being the optical device that is secured to the collimator 40, the radiation treatment system 10 may include a fiber optic bundle 200 as the optical device that is secured to the collimator 40. The collimator 40 may include a channel for accommodating at least a part of the fiber optic bundle 200. In such cases, one end 202 of the fiber optic bundle 200 is configured to capture an image of the target on the skin 28. The fiber optic bundle 200 then transmits the image to an opposite end 204 secured to a camera 100. This configuration is advantageous because the camera 100 may be placed relatively further away from the radiation field, thereby reducing the chance that the camera 100 will be damaged by the radiation from the radiation source 22.

Figure 2C:
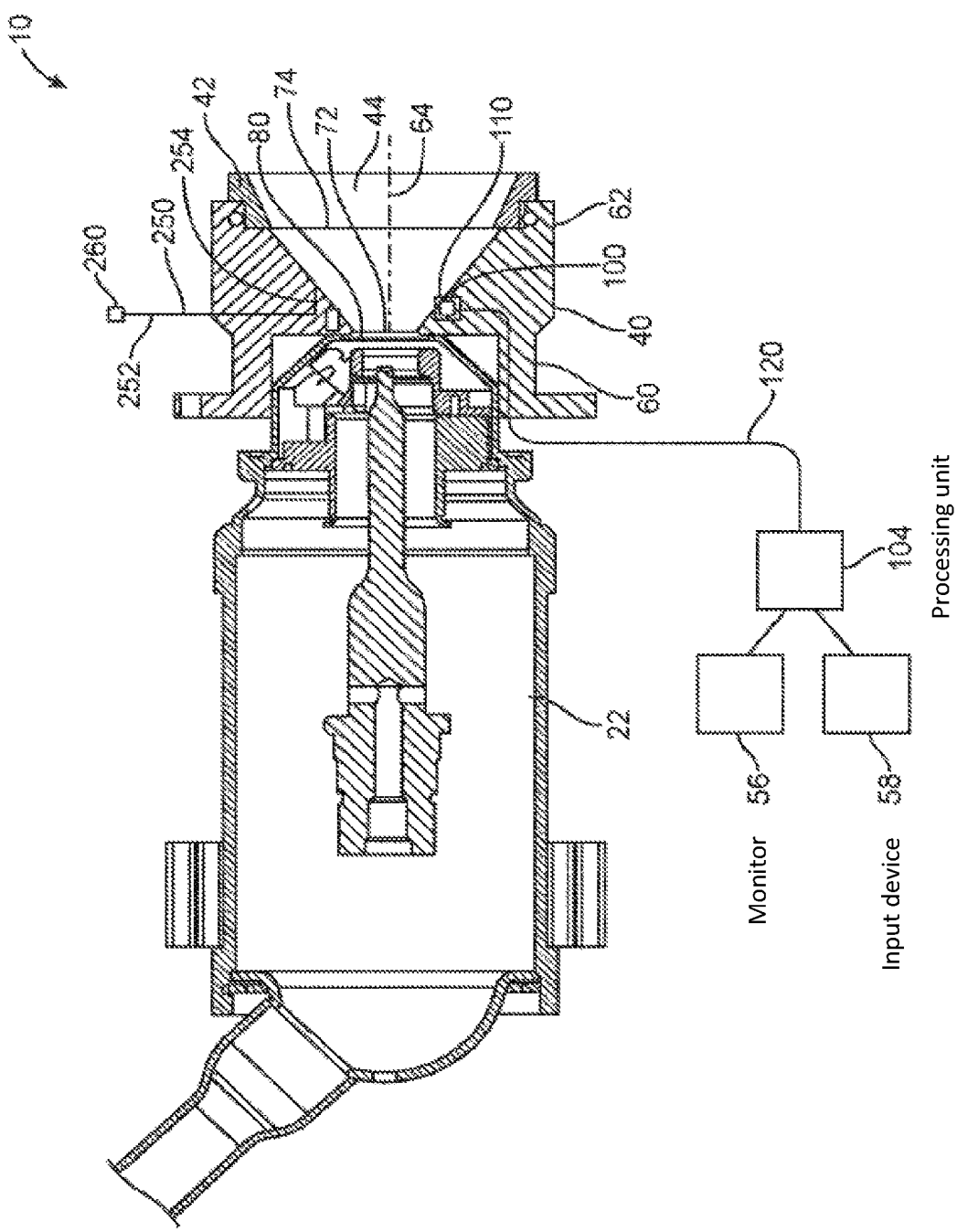
FIG. 2C illustrates another radiation treatment system.

In the above embodiments, the light source 102 is a light bulb mounted at the collimator 40. In other embodiments, the light source 102 may be a fiber optic 250 mounted at the collimator 40 (see FIG. 2C). In the illustrated embodiments, a first end 252 of the fiber optic 250 is mounted to a light bulb 260, which may be a LED light bulb, an incandescent light bulb, or any of other types of light bulbs. Also, a second end 254 of the fiber optic 250 is mounted at the collimator 40. During use, the light bulb 260 supplies light, and the fiber optic 250 transmits the light from the light bulb 260 to an interior space confined by the collimator 40 and the structure 42 defining the aperture 44. The collimator 40 may include a channel for accommodating at least a part of the fiber optic 250. In some embodiments, the light bulb 260 may be coupled to the radiation source 22, or to another component of the radiation treatment system 10. Also, in some embodiments, instead of a single light bulb 260, the radiation treatment system 10 may include multiple light bulbs 260 for providing light to the interior space confined by the collimator 40. In further embodiments, there may be only one light bulb 260, and the fiber optic 250 has a first end 252 coupled to the light bulb 260 for receiving light from the light bulb 260, and multiple second ends 254 which divide the light into multiple parts for delivery into the space confined by the collimator 40. For example, in one implementation the multiple second ends 254 of the fiber optic 250 may be disposed circumferentially around a space defined by the collimator 40. The multiple second ends 254 of the fiber optic 250 may be secured to an interior surface of the collimator 40, or may be accommodated in respective cavities defined by the wall of the collimator 40.

Figure 2D:
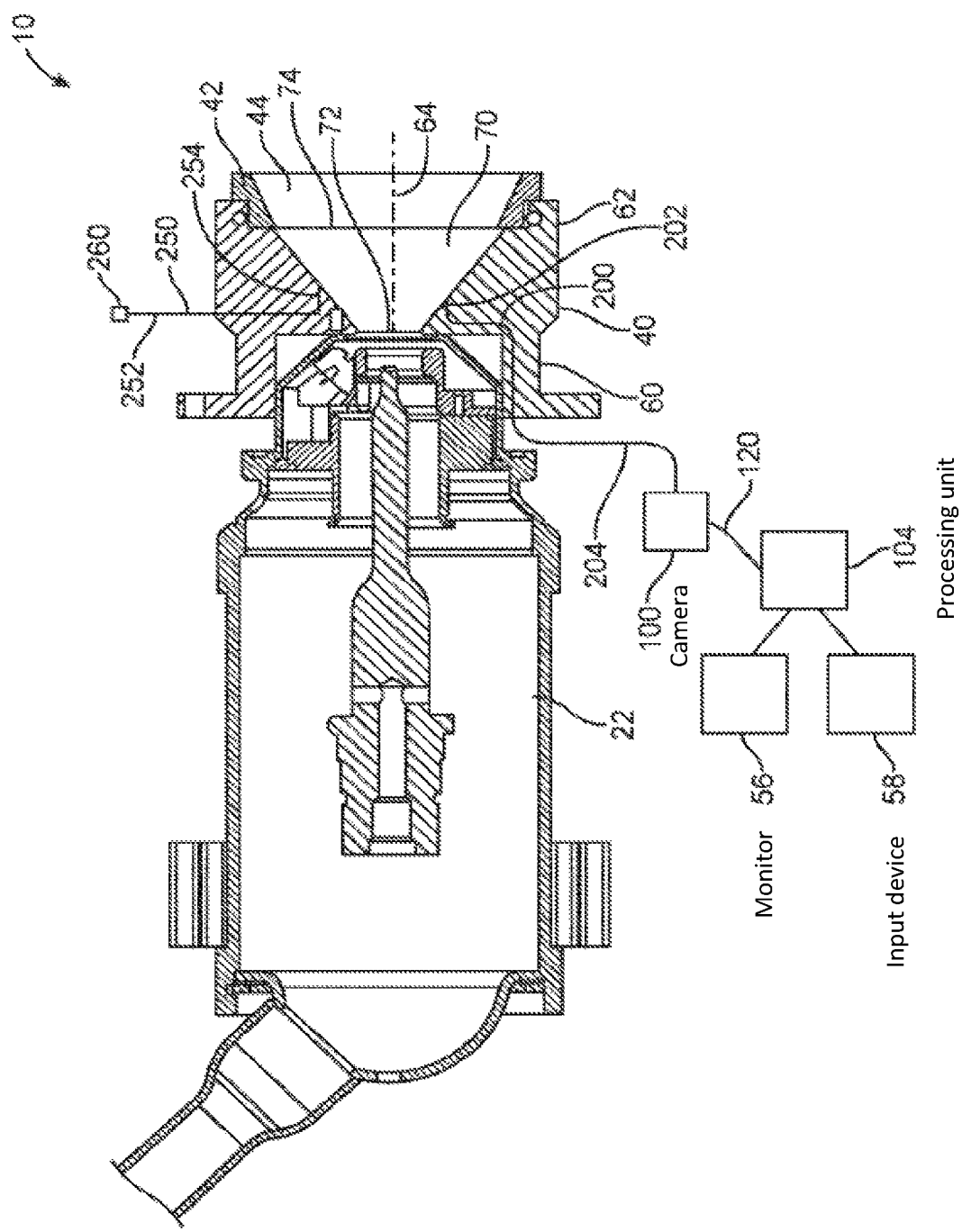
FIG. 2D illustrates another radiation treatment system.

In further embodiments, the radiation treatment system 10 may have a fiber optic bundle 200 with one end 202 secured to the collimator 40, a camera 100 secured to another end 204 of the fiber optic bundle 200, and a fiber optic 250 for transmitting light from a light bulb 260 (FIG. 2D). Thus, in the illustrated embodiments, both the camera 100 and the light bulb 260 are located outside the collimator 40. In some cases, the light bulb 260 may be located at the camera 100. In other cases, the light bulb 260 and the camera 100 may be located at different positions.

In the illustrated embodiments, the end 202 of the fiber optic bundle 200 is configured to capture an image of the target on the skin 28. The fiber optic bundle 200 then transmits the image to an opposite end 204 secured to a camera 100. This configuration is advantageous because the camera 100 may be placed relatively further away from the radiation field, thereby reducing the chance that the camera 100 will be damaged by the radiation from the radiation source 22.

Also, in the illustrated embodiments, a first end 252 of the fiber optic 250 is mounted to a light bulb 260, which may be a LED light bulb, an incandescent light bulb, or any of other types of light bulbs. Also, a second end 254 of the fiber optic 250 is mounted at the collimator 40. During use, the light bulb 260 supplies light, and the fiber optic 250 transmits the light from the light bulb 260 to an interior space confined by the collimator 40. In some embodiments, the light bulb 260 may be coupled to the radiation source 22, or to another component of the radiation treatment system 10. Also, in some embodiments, instead of a single light bulb 260, the radiation treatment system 10 may include multiple light bulbs 260 for providing light to the interior space confined by the collimator 40. In further embodiments, there may be only one light bulb 260, and the fiber optic 250 has a first end 252 coupled to the light bulb 260 for receiving light from the light bulb 260, and multiple second ends 254 which divide the light into multiple parts for delivery into the space confined by the collimator 40. For example, in one implementation the multiple second ends 254 of the fiber optic 250 may be disposed circumferentially around a space defined by the collimator 40. The multiple second ends 254 of the fiber optic 250 may be secured to an interior surface of the collimator 40, or may be accommodated in respective cavities defined by the wall of the collimator 40.

It should be noted that in one or more embodiments described herein, the camera 100 and/or the light source 102 may be detachably secured to the collimator 40. This allows the camera 100 and/or the light source 102 to be detached from the collimator 40 for servicing or for replacement. In other embodiments, the camera 100 and/or the light source 102 may be permanently secured to the collimator 40.

Figure 3:
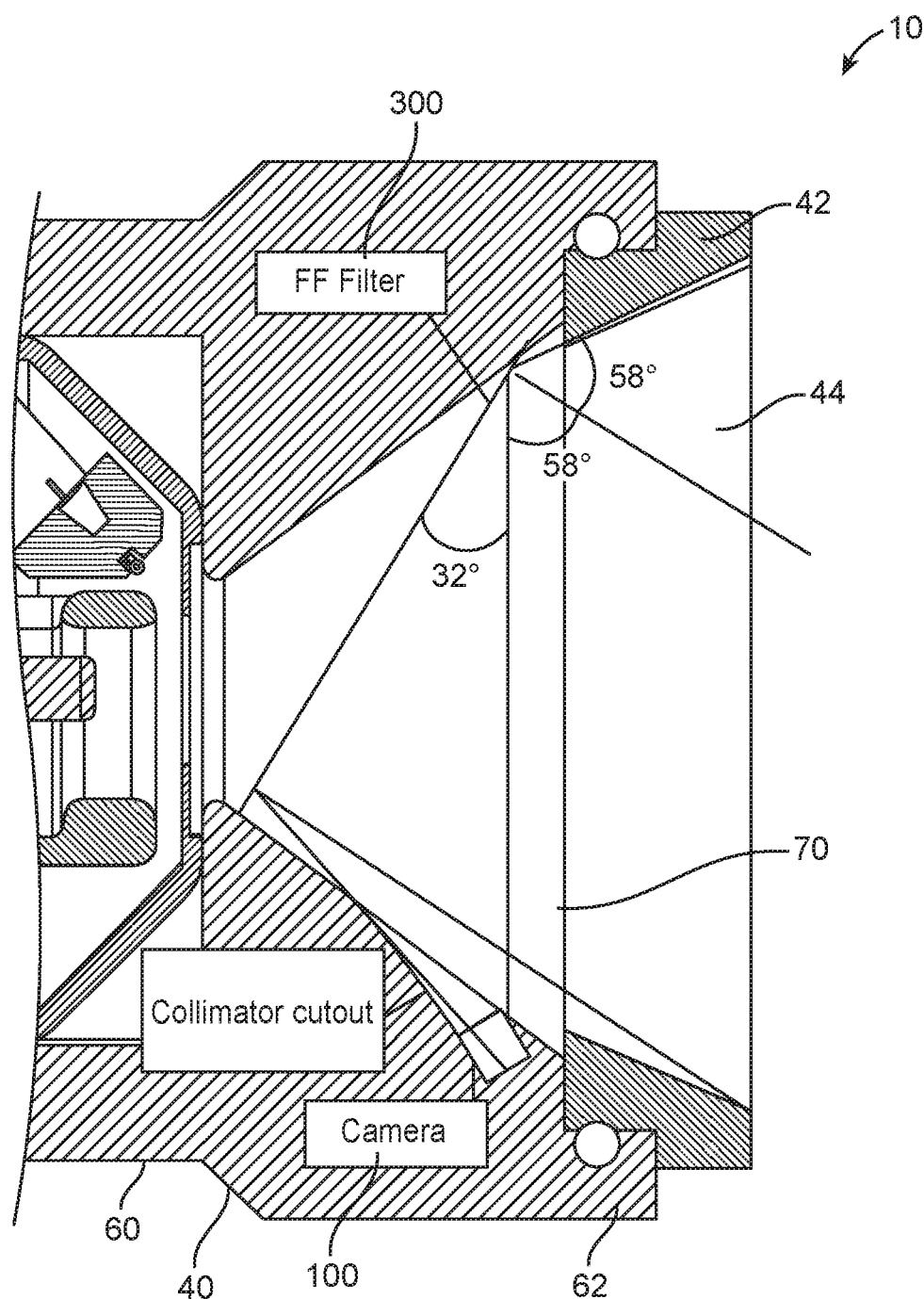
FIG. 3 illustrates a collimator with a flattening filter and an optical device.

In one or more embodiments described herein, the treatment system 10 may further include a flattening filter coupled to the collimator 40. FIG. 3 illustrates another treatment system 10. The treatment system 10 of FIG. 3 is similar to the embodiments described previously, except that the treatment system 10 of FIG. 3 further include a flattening filter 300 coupled to the collimator 40. In particular, the flattening filter 300 is mounted across a cross section in the channel 70. Also, the camera 100 is mounted to the collimator 40 and is oriented so that it is facing proximally towards the flattening filter 300. The flattening filter 300 is made from a transparent material (e.g., a material that is at least partially transparent to radiation), and is configured to modify the radiation beam provided by the radiation source 22 so that the modified radiation beam has a beam profile that is more uniform. A delivered dose of radiation is proportional to the dose rate at the skin surface times the exposure time. The dose rate falls off as the square of the distance from the radiation source 22 and the skin. The distance between the radiation source 22 and the skin (source-to-skin distance SSD) is dependent on the angle ø away from the center beam of the x-rays based on the equation:

$$DoseRate(\emptyset) = \frac{DoseRate\ (\emptyset = 0)}{\cos^2 \emptyset}$$

where ø varies between 0 and the cone angle defined by the aperture's 44 opening. To compensate for this variation in dose rate across the collimator 40, the flattening filter 300 is provided to keep the dose rate at some distance under the skin to be uniform at most or all values of ø.

In the illustrated embodiments, the flattening filter 300 has a mirror surface on one side, so that the camera 100 can view the patient's skin reflected on the mirror surface despite the fact that the camera 100 is facing rearward towards the proximal end.

It should be noted that the components shown in FIG. 3 are not limited to the orientations shown, and that the various components may be adjusted in orientation to achieve a desired effect. For example, the mirror surface at the flattening filter 300 may have an orientation different from that shown, such that the angle of reflection equals the angle of incidence for all rays of interest. In some cases, the mirror surface may be at 45 degrees relative to the axis of the tube, and the camera 100 may be at 90 degrees relative to the axis of the tube. In other cases, the mirror surface and the camera 100 may have other orientations. Also, in the illustrated embodiments, the mirror surface is flat. In other embodiments, the mirror surface may be concave or may have another shape that would allow the image of the treatment area to be "focused" on a certain area. In some cases, the image may be "focused" onto the surface of a CMOS or CCD detector at the camera 100, thereby eliminating the need for any lenses in the camera 100.

Also, in some embodiments, the mirror surface may have a parabola or an offset parabola configuration.

In addition, in some embodiments, the CMOS or CCD detector at the camera 100 may be disposable.

Figure 4:
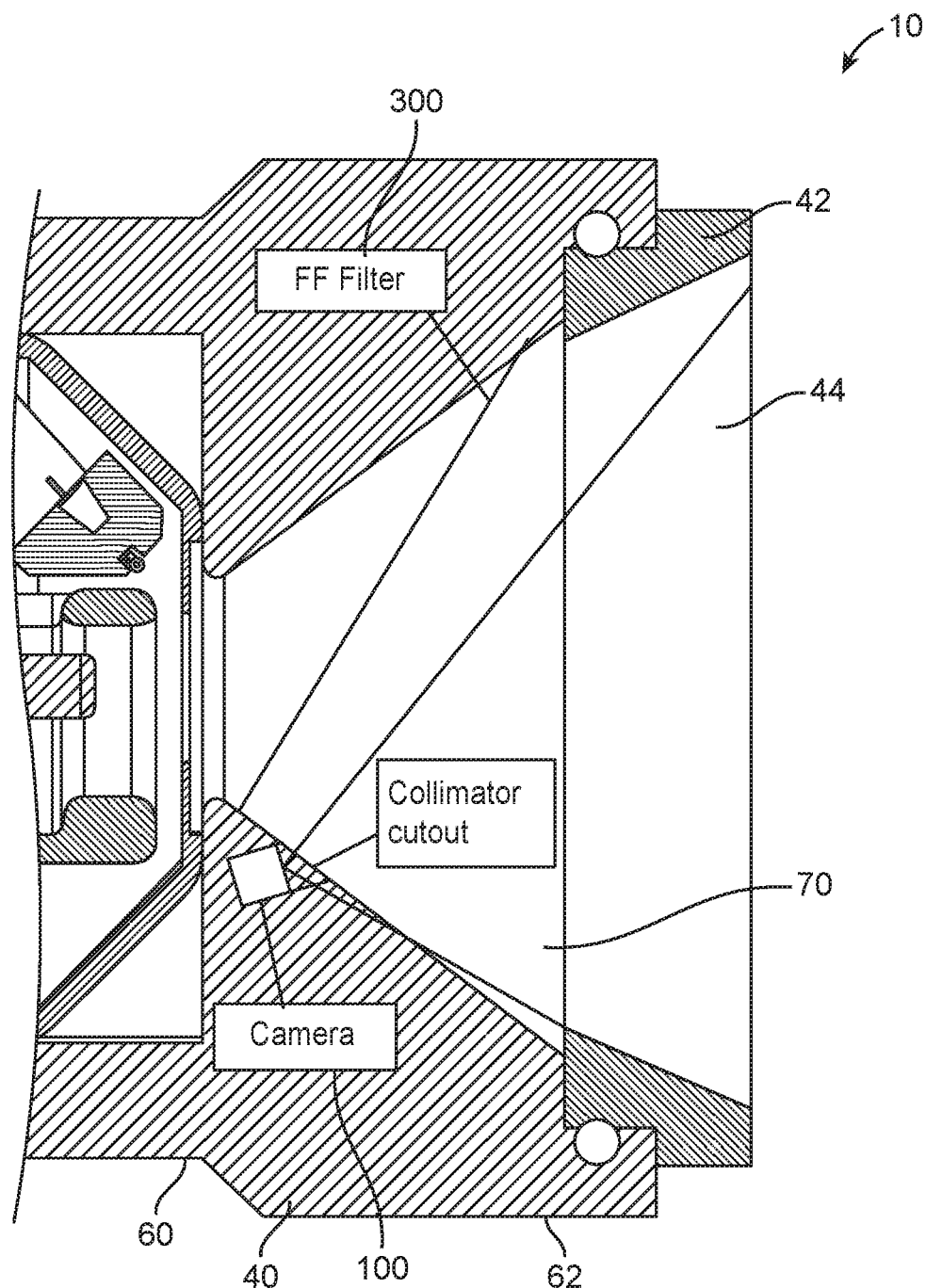
FIG. 4 illustrates another collimator with a flattening filter and an optical device.

In other embodiments, the flattening filter 300 may not have any mirror surface, like that shown in FIG. 4. In such cases, the camera 100 may be oriented so that it can view in a forward direction directly.

Also, in some embodiments, an image provided from the configuration shown in FIG. 4 may be distorted due to keystone effect. In such cases, the distortion may be removed by a distortion removal module that performs image processing to remove such distortion. In some cases, the distortion removal module may be implemented with software.

In the above embodiments, the flattening filter 300 is mounted at an acute angle with respect to a beam axis of the radiation source 22. In other embodiments, like that shown in FIG. 5, the flattening filter 300 may be placed perpendicularly with respect to the axis 64 of the collimator 40. In such cases, the flattening filter 300 would be symmetrical around the central axis of the radiation source 22.

Figure 5:
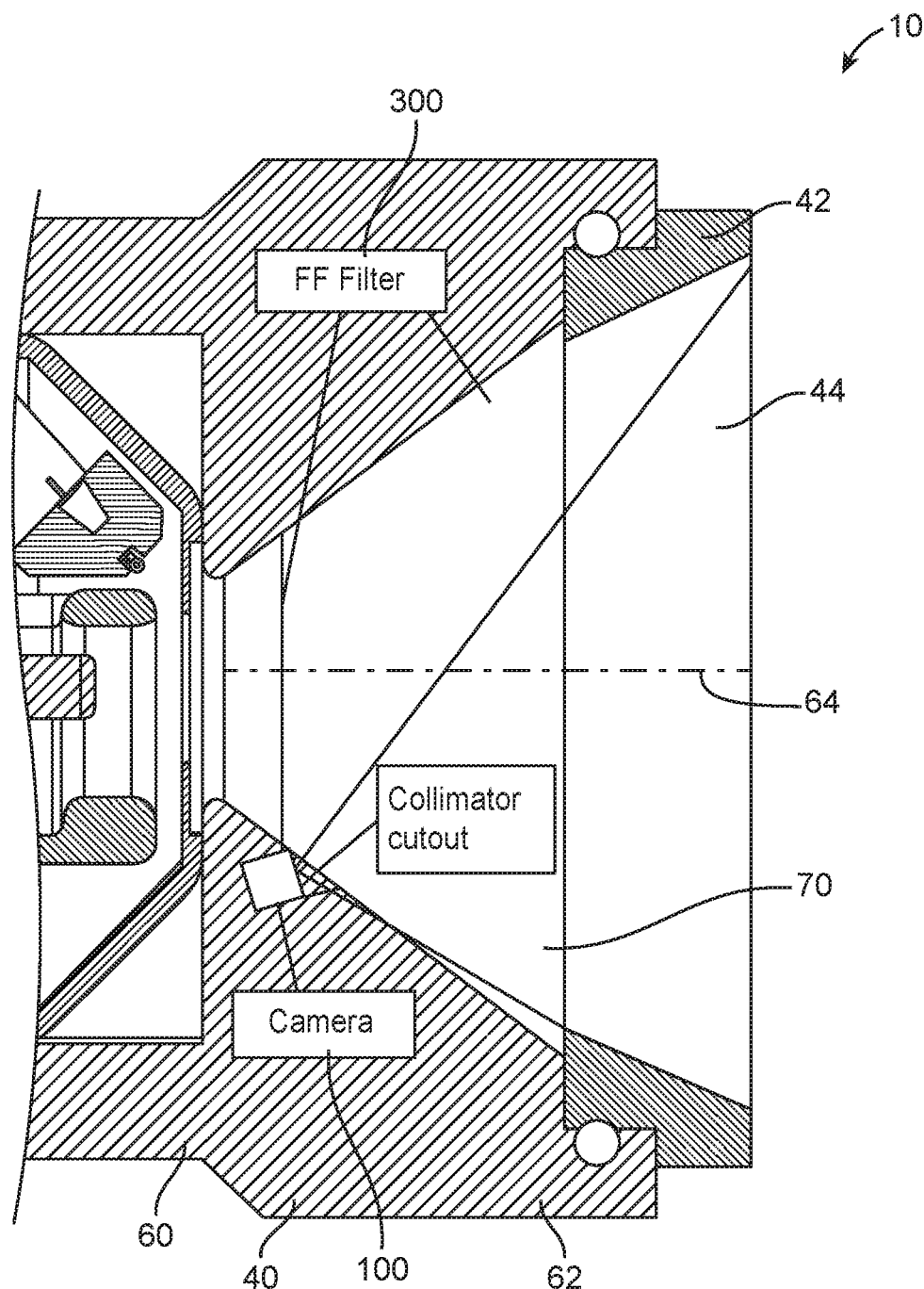
FIG. 5 illustrates another collimator with a flattening filter and an optical device.

Also, in some embodiments, an image provided from the configuration shown in FIG. 5 may be distorted due to keystone effect. In such cases, the distortion may be removed by a distortion removal module that performs image processing to remove such distortion. In some cases, the distortion removal module may be implemented with software.

In some embodiments, the flattening filter 300 may be permanently secured to the collimator 40. In other embodiments, the flattening filter 300 may be detachably secured to the collimator 40. This allows different flattening filters 300 with different respective filtering characteristics to be selectively attached to the collimator 40.

Furthermore, in one or more embodiments described above, the radiation treatment system 10 may optionally further include delivered dose monitoring module configured to monitor delivered radiation dose. For example, the radiation treatment system 10 may include a photodiode on the flattening filter, on the mirror surface, in an ion chamber, or at any of other places at the radiation treatment system 10 to detect delivered radiation. The photodiode may detect delivered radiation, and the processing unit may obtain signals from the photodiode to keep track of the total amount of delivered radiation.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A medical device for treating a skin of a patient, comprising:
    a distal end;
    a radiation source configured to provide radiation;
    a collimator coupled to the radiation source; and
        an optical device for viewing a target area on the skin when the distal end is covering the skin;
    wherein the collimator has a first end, a second end, and a longitudinal axis extending between the first end and the second end, and wherein the collimator further comprises a channel with a cross sectional dimension that increases along at least a part of the longitudinal axis.

2. The medical device of claim 1, further comprising a structure defining an aperture, wherein the structure is configured to couple to the collimator.

3. The medical device of claim 2, wherein the structure is configured to detachably couple to the collimator.

4. The medical device of claim 1, wherein the optical device comprises a camera.

5. The medical device of claim 4, wherein the camera is secured to the collimator.

6. The medical device of claim 5, wherein the camera is secured to an interior surface of the collimator.

7. The medical device of claim 5, wherein the collimator comprises a recess for accommodating the camera.

8. The medical device of claim 4, further comprising a fiber optic bundle coupled to the camera, wherein the fiber optic bundle is secured to the collimator.

9. The medical device of claim 8, wherein the camera is located outside the collimator.

10. The medical device of claim 1, further comprising a light source for providing light to a space located inside the collimator.

11. The medical device of claim 10, wherein the light source comprises a light bulb.

12. The medical device of claim 11, wherein the light bulb is secured to the collimator.

13. The medical device of claim 10, wherein the light source comprises a fiber optic.

14. The medical device of claim 1, further comprising a flattening filter coupled to the collimator.

15. The medical device of claim 14, wherein the flattening filter is made from a transparent material.

16. The medical device of claim 14, wherein the flattening filter is placed perpendicular with respect to a beam axis of the radiation source.

17. The medical device of claim 1, wherein the radiation source comprises a longitudinal axis, and wherein the radiation source comprises an anode and a cathode that is located offset from the longitudinal axis of the radiation source.

18. The medical device of claim 1, wherein the radiation source comprises a window for outputting the radiation, and wherein the collimator has an opening that is aligned with the window of the radiation source.

19. A medical device for treating a skin of a patient, comprising:
    a distal end;
    a radiation source configured to provide radiation;
    a collimator coupled to the radiation source;
    an optical device for viewing a target area on the skin of the patient when the distal end is covering the skin; and
    a flattening filter coupled to the collimator;
    wherein the flattening filter has a mirror surface.

20. A medical device for treating a skin of a patient, comprising:
    a distal end;
    a radiation source configured to provide radiation;
    a collimator coupled to the radiation source;
    an optical device for viewing a target area on the skin when the distal end is covering the skin; and
    a flattening filter coupled to the collimator;
    wherein the flattening filter is placed at an acute angle with respect to a beam axis of the radiation source.

21. A method of treating a skin of a patient, comprising:
    providing a treatment device having a distal end, a radiation source, and a collimator, wherein the distal end is configured for placement over the skin of the patient so that the skin of the patient is covered by the distal end of the treatment device; and
    providing an image of a target on the skin when the distal end of the treatment device is covering the skin of the patient.

22. The method of claim 21, wherein the treatment device further comprises a structure defining an aperture, the structure coupled to the collimator.

23. The method of claim 22, further comprising providing one or more additional images of the target when the target is being treated by the radiation.

24. The method of claim 21, further comprising using the radiation source to deliver treatment radiation at the target on the skin.

25. The method of claim 21, further comprising providing light to a space located inside the collimator.

* * * * *